(12) United States Patent
Hyuga (10) Patent No.: US 8,216,142 B2
(45) Date of Patent: Jul. 10, 2012

(54) ULTRASONIC PROBE, ULTRASONIC DIAGNOSTIC APPARATUS AND ULTRASONIC ENDOSCOPIC APPARATUS

(75) Inventor: Hiroaki Hyuga, Kaisei-machi (JP)

(73) Assignee: FUJIFILM Corporation, Tokyo (JP)

( * ) Notice: Subject to any disclaimer, the term of this patent is extended or adjusted under 35 U.S.C. 154(b) by 527 days.

(21) Appl. No.: 12/434,881

(22) Filed: May 4, 2009

(65) Prior Publication Data
US 2009/0287086 A1      Nov. 19, 2009

(30) Foreign Application Priority Data
May 19, 2008      (JP) .................................. 2008-130755

(51) Int. Cl.
*A61B 8/00*      (2006.01)
(52) U.S. Cl. ........ 600/439; 600/407; 600/437; 600/438; 600/443
(58) Field of Classification Search .................. 600/407, 600/437, 438, 439, 443
See application file for complete search history.

(56) References Cited

U.S. PATENT DOCUMENTS

| | | | | |
|---|---|---|---|---|
| 4,443,731 | A | * | 4/1984 | Butler et al. ................... 310/334 |
| 7,598,658 | B2 | * | 10/2009 | Takeuchi et al. .............. 310/334 |
| 2002/0098968 | A1 | * | 7/2002 | Takahashi et al. ............ 501/137 |
| 2003/0048037 | A1 | * | 3/2003 | Boyd ............................. 310/318 |
| 2006/0100522 | A1 | * | 5/2006 | Yuan et al. ..................... 600/466 |
| 2008/0218559 | A1 | * | 9/2008 | Fujii et al. ........................ 347/68 |
| 2008/0289420 | A1 | * | 11/2008 | Cochran et al. ................. 73/596 |
| 2011/0021916 | A1 | * | 1/2011 | Morita .......................... 600/443 |

FOREIGN PATENT DOCUMENTS

| | | |
|---|---|---|
| JP | 5-51222 A | 3/1993 |
| JP | 6-14398 A | 1/1994 |

OTHER PUBLICATIONS

Michael J. Zipparo, "Multilayer Ultrasound Imaging Arrays showing Improved Thermal Performance", IEEE Ultrasonics Symposium, 2005, pp. 2235-2238.

* cited by examiner

*Primary Examiner* — Brian Casler
*Assistant Examiner* — Joel Lamprecht
(74) *Attorney, Agent, or Firm* — Sughrue Mion, PLLC (57) ABSTRACT

An ultrasonic probe in which a balance between basic performance and suppression of heat generation is achieved by suppressing heat generation of the ultrasonic probe without degrading sensitivity and relative bandwidth of the ultrasonic probe in transmission and reception of ultrasonic waves. The ultrasonic probe includes at least one vibrator for transmitting and receiving ultrasonic waves, the at least one vibrator including a piezoelectric material in which a piezoelectric strain constant d33 is equal to or less than 500 pm/V and a product of the piezoelectric strain constant d33 and a piezoelectric voltage constant g33 is equal to or more than 7000× $10^{-15}$ m²/N, at least one acoustic matching layer provided on a first surface of the at least one vibrator, and a backing material provided on a second surface opposite to the first surface of the at least one vibrator.

11 Claims, 11 Drawing Sheets

| | PIEZO-ELECTRIC MATERIAL | d33 (pm/V) | g33 (×10⁻³ v·m/N) | d33 × g33 (×10⁻¹⁵ m²/N) | Qm | ΔT(°C) | SENSITIVITY (dB) | RELATIVE BANDWIDTH (%) | EVALUATION |
|---|---|---|---|---|---|---|---|---|---|
| CONVENTIONAL EXAMPLE 1 | A | 670 | 17.9 | 11993 | 65 | 2.7 | −70.5 | 60 | A conventionally and generally used material: Sensitivity and band are good, but the amount of heat generation is large. |
| CONVENTIONAL EXAMPLE 2 | B | 710 | 13.9 | 9869 | 24 | 2.9 | −71.4 | 60.3 | A conventionally and generally used material: Sensitivity and band are good, but the amount of heat generation is large. |
| CONVENTIONAL EXAMPLE 3 | C | 670.7 | 16.5 | 11066.55 | 51.7 | 3.4 | −70.1 | 61.5 | A conventionally and generally used material: Sensitivity and band are good, but the amount of heat generation is large. |
| CONVENTIONAL EXAMPLE 4 | D | 635 | 13.2 | 8382 | 70 | 3.2 | −73.2 | 56.2 | A conventionally and generally used material: Sensitivity and band are good, but the amount of heat generation is large. |
| CONVENTIONAL EXAMPLE 5 | E | 660 | 16.3 | 10758 | 60 | 3.1 | −69.8 | 62.4 | A conventionally and generally used material: Sensitivity and band are good, but the amount of heat generation is large. |
| COMPARATIVE EXAMPLE 1 | F | 116 | 16 | 1856 | 1880 | 0.3 | −83.6 | 45.3 | Small amount of heat generation, low sensitivity, narrow band. |
| COMPARATIVE EXAMPLE 2 | G | 280 | 16.5 | 4620 | 1350 | 0.8 | −79 | 49.8 | Small amount of heat generation, low sensitivity, narrow band. |
| COMPARATIVE EXAMPLE 3 | H | 154 | 32.4 | 4989.6 | 1900 | 0.5 | −75.2 | 53.2 | Small amount of heat generation, low sensitivity, narrow band. |
| COMPARATIVE EXAMPLE 4 | I | 110 | 33.7 | 3707 | 1700 | 0.4 | −77.6 | 47.7 | Small amount of heat generation, low sensitivity, narrow band. |
| WORKING EXAMPLE 1 | J | 367 | 29.2 | 10716.4 | 1200 | 1 | −70.2 | 50.1 | Small amount of heat generation, good sensitivity, narrow band. |
| WORKING EXAMPLE 2 | K | 310 | 23.4 | 7254 | 2500 | 1 | −71.6 | 51.9 | Small amount of heat generation, good sensitivity, narrow band. |
| WORKING EXAMPLE 3 | L | 315 | 25 | 7875 | 2000 | 0.9 | −72 | 52.3 | Small amount of heat generation, good sensitivity, narrow band. |
| WORKING EXAMPLE 4 | M | 333 | 32.1 | 10689.3 | 90 | 1.4 | −71 | 60.8 | Small amount of heat generation, good sensitivity, good band. |
| WORKING EXAMPLE 5 | N | 490 | 23.2 | 11368 | 70 | 1.7 | −72.7 | 61.1 | Small amount of heat generation, good sensitivity, good band. |
| WORKING EXAMPLE 6 | O | 420 | 23.3 | 9786 | 60 | 1.6 | −72.7 | 63 | Small amount of heat generation, good sensitivity, good band. |

FIG.3

| WORKING EXAMPLE 1 | J | $(Pb_{0.95}Sr_{0.05})(Zr_{0.54}Ti_{0.46})O_3:Mn_{0.006},Sb_{0.006},Nb_{0.007}$ |
|---|---|---|
| WORKING EXAMPLE 2 | K | $Pb(Zr_{0.51}Ti_{0.49})O_3:Nb_{0.1},Mn_{0.015},Co_{0.016}$ |
| WORKING EXAMPLE 3 | L | $Pb(Zr_{0.51}Ti_{0.49})O_3:Nb_{0.05},Mn_{0.017},Ag_{0.011},Sr_{0.054}$ |
| WORKING EXAMPLE 4 | M | $(Pb_{0.96}Ba_{0.03}Sr_{0.01})(Zr_{0.54}Ti_{0.46})O_3:Sb_{0.006},Nb_{0.007}$ |
| WORKING EXAMPLE 5 | N | $(Pb_{0.94}Ba_{0.02}Sr_{0.04})(Zr_{0.53}Ti_{0.47})O_3:Nb_{0.016},Sb_{0.007}$ |
| WORKING EXAMPLE 6 | O | $(Pb_{0.95}Sr_{0.05})(Zr_{0.53}Ti_{0.47})O_3:Nb_{0.025}$ |

| | VIBRATOR STRUCTURE | PIEZO-ELECTRIC MATERIAL | SENSITIVITY (dB) | RELATIVE BANDWIDTH (%) | ΔT(°C) |
|---|---|---|---|---|---|
| COMPARATIVE EXAMPLE 5 | THREE-LAYERED STRUCTURE | C | −61.5 | 70.5 | 50 |
| WORKING EXAMPLE 7 | THREE-LAYERED STRUCTURE | N | −60.1 | 70.1 | 25 |
| WORKING EXAMPLE 8 | THREE-LAYERED STRUCTURE | O | −62.7 | 73 | 22 |
| WORKING EXAMPLE 9 | THREE-LAYERED STRUCTURE | L | −61.9 | 60 | 17 |
| WORKING EXAMPLE 10 | THREE-LAYERED STRUCTURE USING COMPOSITE MATERIAL | O | −54.1 | 98 | 13.2 |

ULTRASONIC PROBE, ULTRASONIC DIAGNOSTIC APPARATUS AND ULTRASONIC ENDOSCOPIC APPARATUS

BACKGROUND OF THE INVENTION

1. Field of the Invention

The present invention relates to an ultrasonic probe to be used for extra-cavity scanning or intra-cavity scanning of an object to be inspected. Further, the present invention relates to an ultrasonic diagnostic apparatus including such an ultrasonic probe and an ultrasonic diagnostic apparatus main body, and an ultrasonic endoscopic apparatus including an ultrasonic endoscope having the ultrasonic probe and an ultrasonic endoscopic apparatus main body.

2. Description of a Related Art

In medical fields, various imaging technologies have been developed in order to observe the interior of an object to be inspected and make diagnoses. Especially, ultrasonic imaging for acquiring interior information of the object by transmitting and receiving ultrasonic waves enables image observation in real time and provides no exposure to radiation unlike other medical image technologies such as X-ray photography or RI (radio isotope) scintillation camera. Accordingly, ultrasonic imaging is utilized as an imaging technology at a high level of safety in a wide range of departments including not only the fetal diagnosis in the obstetrics, but gynecology, circulatory system, digestive system, and so on.

The ultrasonic imaging is an image generation technology utilizing the nature of ultrasonic waves that the ultrasonic waves are reflected at a boundary between regions with different acoustic impedances (e.g., a boundary between structures). Typically, an ultrasonic diagnostic apparatus (or referred to as an ultrasonic imaging apparatus or an ultrasonic observation apparatus) is provided with an ultrasonic probe to be used in contact with the object or ultrasonic probe to be used by being inserted into a body cavity of the object. Alternatively, an ultrasonic endoscope in combination of an endoscope for optically observing the interior of the object and an ultrasonic probe for intracavity is also used.

In the ultrasonic probe, generally, a piezoelectric vibrator having electrodes formed on both ends of a piezoelectric material is used as an ultrasonic transducer for transmitting and receiving ultrasonic waves. When a voltage is applied to the electrodes of the vibrator, the piezoelectric material expands and contracts to generate ultrasonic waves. Further, plural vibrators are one-dimensionally or two-dimensionally arranged and the vibrators are driven by drive signals provided with predetermined delays, and thereby, an ultrasonic beam can be formed toward a desired direction. On the other hand, the vibrator receives the propagating ultrasonic waves, expands and contracts, and generates an electric signal. The electric signal is used as a reception signal of ultrasonic waves.

As a guideline of a piezoelectric material to be used for a conventional piezoelectric vibrator, one having a large vibration amplitude (large piezoelectric strain constant d33) and generating a small amount of heat at transmission of ultrasonic waves has been desired. Further, for reducing heat generation, it has been considered important that the mechanical quality factor Qm is large and the dielectric loss tan δe is small (see the following documents).

As a related technology, Japanese Patent Application Publication JP-A-5-51222 discloses a piezoelectric porcelain material that provides large vibration and generates a small amount of heat in use as an ultrasonic vibrator. In the piezoelectric porcelain material, all of the mechanical quality factor, the piezoelectric constant, and the dielectric loss are above certain levels.

Further, Japanese Patent Application Publication JP-A-6-14398 discloses an ultrasonic probe for suppressing an amount of heat generated when driven and preventing the characteristic degradation thereby. According to JP-A-6-14398, in an ultrasonic probe in which a piezoelectric element as a source of ultrasonic waves is fixed onto a backing material, an acoustic matching layer is provided on the front face of the piezoelectric element, and they are enclosed in a case, the dielectric loss of the piezoelectric element is 1.6% or less and the amount of heat generated at driving of the piezoelectric element is lowered.

Furthermore, Michael J. Zipparo, "Multilayer Ultrasound Imaging Arrays showing Improved Thermal Performance", Proc. 2005 IEEE Ultrasonics Symposium, pp. 2235-2238 describes multilayer ultrasound imaging arrays designed to have improved acoustic power delivery capability without sacrificing imaging performance. In the document, Table 1 shows physical properties of PZT materials used for single layer ultrasound imaging arrays, and Table 2 shows physical properties of PZT materials used for multilayer ultrasound imaging arrays.

SUMMARY OF THE INVENTION

However, when a material having a large piezoelectric strain constant d33 is selected for further improvement of sensitivity of the ultrasonic probe, there is a problem that the heat generation at transmission of ultrasonic waves increases. On the other hand, when a material having a large mechanical quality factor Qm is selected for reduction of heat generation, there is a problem that the trailing of the pulse waveform of ultrasonic waves is increased and the relative bandwidth is narrowed. That is, in the conventional ultrasonic probe, a good valance between the basic performance (sensitivity and relative bandwidth) of the ultrasonic probe and the suppression of heat generation of the ultrasonic probe has not been achieved.

Accordingly, in view of the above-mentioned points, a purpose of the present invention is to provide an ultrasonic probe in which a balance between basic performance and suppression of heat generation is achieved by suppressing heat generation of the ultrasonic probe without degrading sensitivity and relative bandwidth of the ultrasonic probe in transmission and reception of ultrasonic waves.

In order to accomplish the purpose, an ultrasonic probe according to one aspect of the present invention includes at least one vibrator for transmitting and receiving ultrasonic waves, the at least one vibrator including a piezoelectric material in which a piezoelectric strain constant d33 is not larger than 500 pm/V and a product of the piezoelectric strain constant d33 and a piezoelectric voltage constant g33 is not less than $7000 \times 10^{-15}$ m²/N, at least one acoustic matching layer provided on a first surface of the at least one vibrator, and a backing material provided on a second surface opposite to the first surface of the at least one vibrator.

Further, an ultrasonic diagnostic apparatus according to one aspect of the present invention includes the ultrasonic probe according to the present invention, drive signal supply means for supplying at least one drive signal to the at least one vibrator, and signal processing means for processing at least one reception signal outputted from the at least one vibrator to generate image data representing an ultrasonic image.

Furthermore, an ultrasonic endoscopic apparatus according to one aspect of the present invention includes an ultrasonic endoscope including the ultrasonic probe according to the present invention, drive signal supply means for supplying at least one drive signal to the at least one vibrator, and signal processing means for processing at least one reception signal outputted from the at least one vibrator to generate image data representing an ultrasonic image.

According to one aspect of the present invention, since the vibrator is formed by using the piezoelectric material in which the piezoelectric strain constant d33 not lager than 500 pm/V and the product of the piezoelectric strain constant d33 and a piezoelectric voltage constant g33 is not less than 7000× $10^{-15}$ m$^2$/N, the ultrasonic probe can be provided in which a balance between basic performance and suppression of heat generation is achieved by suppressing heat generation of the ultrasonic probe without degrading the sensitivity and relative bandwidth of the ultrasonic probe in transmission and reception of ultrasonic waves.

BRIEF DESCRIPTION OF THE DRAWINGS

FIG. 2 shows measurement results of piezoelectric performances of various kinds of piezoelectric materials and properties of ultrasonic probes fabricated by using those piezoelectric materials;

DESCRIPTION OF THE PREFERRED EMBODIMENTS

Hereinafter, preferred embodiments of the present invention will be explained in detail with reference to the drawings. The same reference numerals will be assigned to the same component elements and the description thereof will be omitted.

Figure 1:
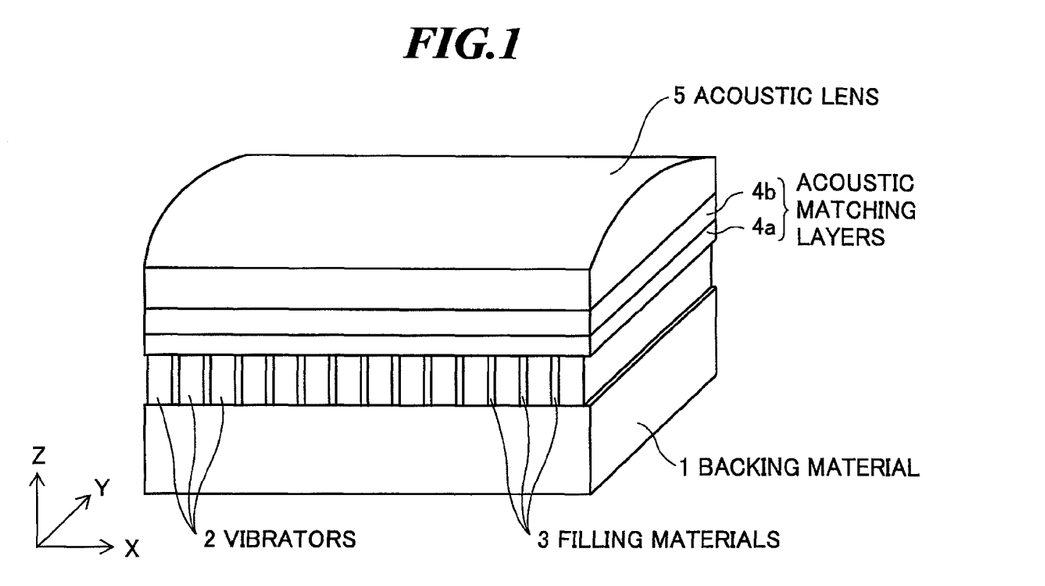
FIG. 1 is a perspective view schematically showing an internal structure of an ultrasonic probe according to the first embodiment of the present invention.

FIG. 1 is a perspective view schematically showing an internal structure of an ultrasonic probe according to the first embodiment of the present invention. The ultrasonic probe is used in contact with an object to be inspected for extracavitary scanning, or used by being inserted into a body cavity of the object for intracavitary scanning.

As shown in FIG. 1, the ultrasonic probe has a backing material 1, plural ultrasonic transducers (piezoelectric vibrators) 2 provided on the backing material 1, filling materials 3 of epoxy resin or the like filling between and around the plural vibrators 2 for reducing the interference between the vibrators and suppressing the vibration of the vibrators in the lateral direction and allowing the vibrators to vibrate only in the longitudinal direction, at least one acoustic matching layer (two acoustic matching layers 4a and 4b are shown in FIG. 1) provided on the piezoelectric vibrators 2, and an acoustic lens 5 provided on the acoustic matching layers according to need.

In the embodiment, the plural piezoelectric vibrators 2 arranged in an azimuth direction (X-axis direction) form a one-dimensional vibrator array, however, the present invention can be applied to an ultrasonic probe having a two-dimensional vibrator array in which plural piezoelectric vibrators are two-dimensionally arranged or an ultrasonic probe having one piezoelectric vibrator.

When the ultrasonic transmitting and receiving operation of the ultrasonic probe is divided into two of a transmission process and a reception process, heat is generated mainly in the transmission process. The inventor of the present application has found that the heat generation in the transmission process is caused by the vibration amplitude of the piezoelectric material itself and the larger the piezoelectric strain constant d33 of the material, the larger the amount of heat generation. Further, it is considered that the transmission performance of the ultrasonic probe is proportional to the piezoelectric strain constant d33 that indicates the magnitude of the displacement when a voltage is applied, and the reception performance of the ultrasonic probe is proportional to the piezoelectric voltage constant g33 that indicates the magnitude of a voltage generated when pressure is applied.

Therefore, the heat generation of the ultrasonic probe can be suppressed while the basic performance of the ultrasonic probe in transmission and reception of ultrasonic waves is maintained by reducing vibration amplitude at transmission to reduce the transmission acoustic power and improving reception sensitivity. Specifically, for reduction of heat generation, it is effective that the piezoelectric strain constant d33 is reduced, desirably 0<d33≦500 pm/V, for example. On the other hand, for improvement of reception sensitivity, it is effective that the piezoelectric voltage constant g33 is increased. In order to reduce the heat generation while maintaining the transmission and reception sensitivity, for example, it is desirable to hold 7000×$10^{-15}$ m$^2$/N≦d33× g33≦20000×$10^{-15}$ m$^2$/N, for example. Further, in order to reduce the heat generation and maintain the relative bandwidth (depth resolving power), it is effective that the mechanical quality factor Qm is made small to some degree, desirably 10≦Qm≦100, for example.

The ultrasonic probe shown in FIG. 1 is actually fabricated by using various kinds of piezoelectric materials, and the properties are measured. The results are explained as below. In the ultrasonic probe shown in FIG. 1, the length in the X-axis direction is 50 mm, and the length in the Y-axis direction is 4 mm. Further, in each vibrator 2, the length in the Y-axis direction is 4 mm, the length in the X-axis direction is 110 μm, and the length in the Z-axis direction is 300 μm.

In measurement of sensitivity and relative bandwidth, only one vibrator of one-dimensional vibrator array is driven and ultrasonic waves are transmitted and received in a water tank, and the properties thereof are measured. The center frequency of the ultrasonic waves to be transmitted and received is 6 MHz, and an ultrasonic transmitting and receiving apparatus (Model 5900 manufactured by Panametrics) is used for generating a drive signal.

In measurement of temperature rise ΔT, for the purpose of relative comparison, a function generator (Model 33220A manufactured by Agilent) is used for applying a sine wave in a voltage range of −3V to +3V to one vibrator, and the surface temperature rise is measured by using a noncontact thermometer in the air at room temperature of 23° C. The surface temperature rises with time immediately after the driving of vibrator is started and nearly saturated in about 10 minutes, and thus, the temperature is measured after the saturation.

FIG. 2 shows measurement results of piezoelectric performances of various kinds of piezoelectric materials and properties of ultrasonic probes fabricated by using those piezoelectric materials. In FIG. 2, piezoelectric strain constants d33, piezoelectric voltage constants g33, respective products d33×g33 of piezoelectric strain constants and piezoelectric voltage constants, and mechanical quality factors Qm of the various kinds of piezoelectric materials, and temperature rises ΔT, transmission and reception sensitivity, relative bandwidths of the ultrasonic probes fabricated by using those piezoelectric materials are shown. The relative bandwidth $f_{BW}$(%) is expressed by the following equation.

$$f_{BW}(\%)=100\times(f_H-f_L)/f_C$$

where frequencies $f_H$ and $f_L$ are two frequencies at which the sound pressure attenuates from the peak value by 6 dB ($f_L<f_H$), and frequency $f_C$ is a center frequency between the frequency $f_H$ and the frequency $f_L$.

Conventional examples 1-5 are ultrasonic probes using piezoelectric materials A-E that have been typically used for conventional ultrasonic probes, and the basic performance (sensitivity and relative bandwidth) is good, but the amount of heat generation is large and the temperature rise is large. The Comparative examples 1-4 are ultrasonic probes using piezoelectric materials F-I, and the temperature rise is suppressed but the basic performance is low. Working examples 1-6 of the present invention are ultrasonic probes using piezoelectric materials J-O, and maintenance of the basic performance and suppression of the temperature rise is balanced.

Figure 3:
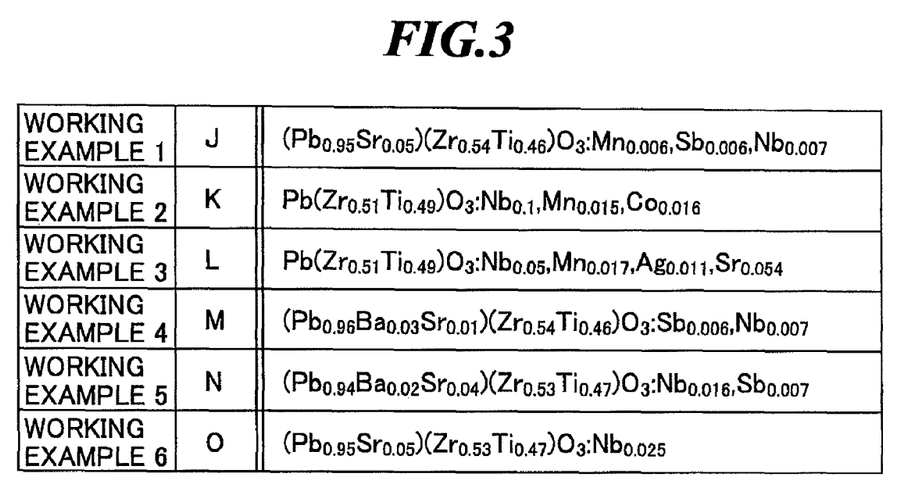
FIG. 3 shows compositions of the piezoelectric materials J-O used in working examples 1-6 of the present invention.

FIG. 3 shows compositions of the piezoelectric materials J-O used in working examples 1-6 of the present invention. Among them, the piezoelectric materials J, K, L are modifications of hard type PZT (Pb (lead) zirconate titanate) and the piezoelectric materials M, N, O are modifications of soft type PZT.

The piezoelectric materials used in the experiment are manufactured according to a widely known general ceramics manufacturing method, called a solid-state thermochemical reaction method. The manufacturing method will be explained as below. At step (1), basic ingredients are oxidized or carbonated and the oxides or the carbonates are compounded and mixed at a desired molecular ratio, and thereby, a raw material is fabricated. At step (2), the raw material is preliminarily burned and dissolved in an atmosphere at a temperature of 800° C. to 1000° C., and the raw material is turned into a solid solution according to the solid-state thermochemical reaction. At step (3), the raw material obtained at step (2) is crushed into fine particles, and then, the process returns to step (2). Steps (2) and (3) are repeated at plural times, and finally, a perovskite single phase is formed. At step (4), dry molding is performed on the fine particles obtained at step (3) at pressure of 50 MPa to 300 MPa, and then, chemical reaction of the unreacted part is completed by full-scale burning at a temperature of 1150° C. to 1350° C. and the fine particles are sintered for high density. At step (5), the final form is shaped by cutting and grinding. At step (6), electrodes are formed by sputtering, and then, polarization processing is performed thereon. Thus, manufacturing of a piezoelectric material is completed.

Referring to FIG. 2 again, working examples 1-3 using the piezoelectric materials J, K, L are suitable for limited uses because the amount of heat generation is small and the sensitivity is good, but the relative bandwidth is relatively narrow. On the other hand, working examples 4-6 using the piezoelectric materials M, N, O are suitable for ultrasonic probes for wide band because the amount of heat generation is small and the sensitivity is good, and the relative bandwidth is good.

Figure 4:
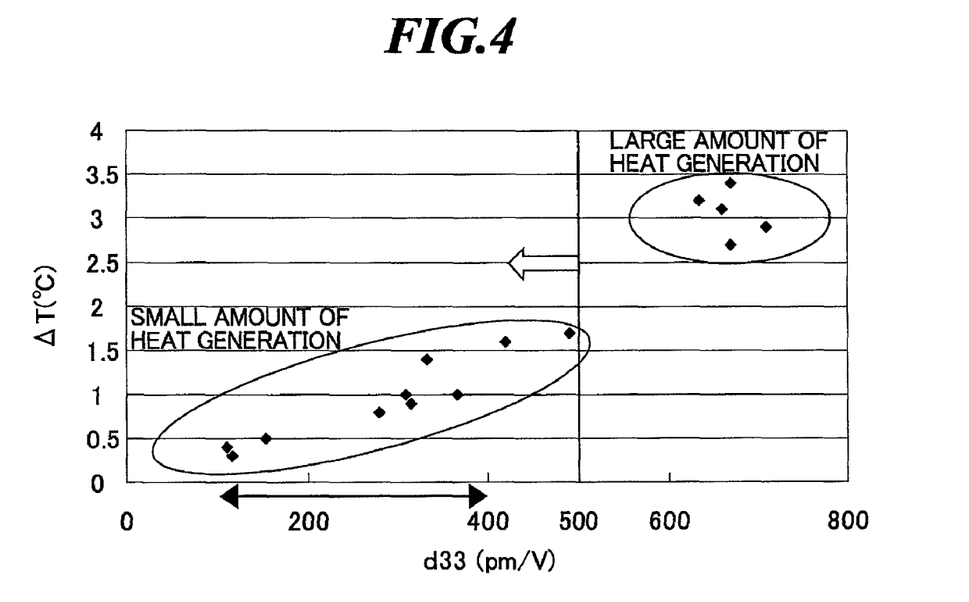
FIG. 4 shows a relationship between the piezoelectric strain constant d33 and the temperature rise ΔT.

FIG. 4 shows a relationship between the piezoelectric strain constant d33 and the temperature rise ΔT. As shown in FIG. 4, the temperature rise ΔT is nearly proportional to the piezoelectric strain constant d33. By using a piezoelectric material having the piezoelectric strain constant d33 of 500 pm/V or less, the temperature rise ΔT can be reduced by nearly half compared to that in the conventional example. More preferably, it is recommended to use a piezoelectric material having the piezoelectric strain constant d33 of 400 pm/V or less.

Figure 5:
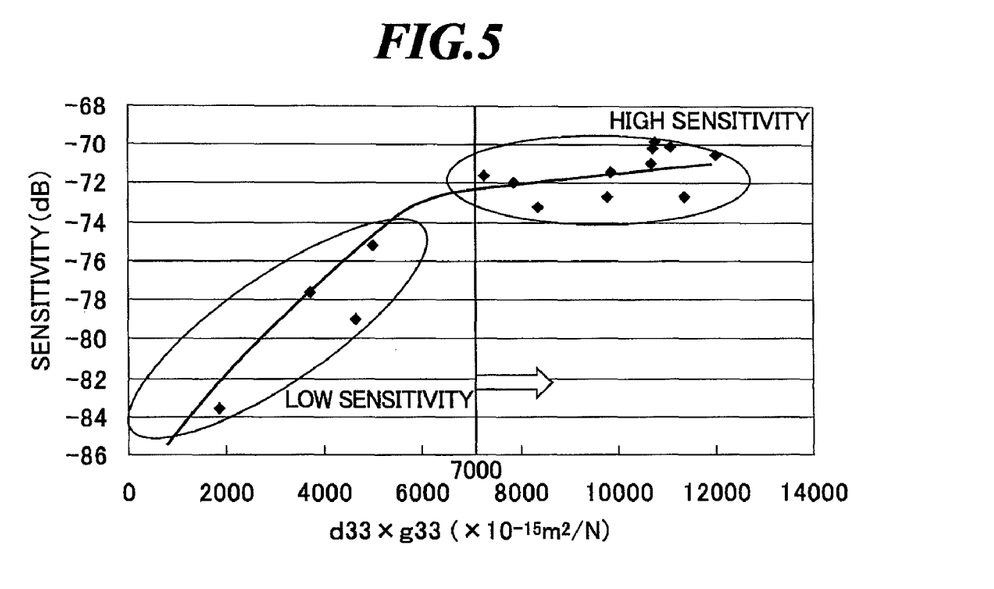
FIG. 5 shows a relationship between the product d33×g33 of piezoelectric strain constant and piezoelectric voltage constant and the transmission and reception sensitivity.

FIG. 5 shows a relationship between the product d33×g33 of piezoelectric strain constant and piezoelectric voltage constant and the transmission and reception sensitivity. As shown in FIG. 5, high sensitivity is maintained if d33×g33 is 7000×$10^{-15}$ m$^2$/N or more, however, the sensitivity reduction is drastic if d33×g33 is less than 7000×$10^{-15}$ m$^2$/N. Therefore, the value of d33×g33 is suitably set to 7000×$10^{-15}$ m$^2$/N or more, preferably 9000×$10^{-15}$ m$^2$/N or more, more preferably 10000×$10^{-15}$ m$^2$/N or more, and even more preferably 11000×$10^{-15}$ m$^2$/N or more.

However, it is not appropriate that the value of d33 is too large, and the upper limit of the value of d33×g33 is about 20000×$10^{-15}$ m$^2$/N. Further, the value of piezoelectric voltage constants g33 is suitably set to 14×$10^{-3}$ Vm/N or more, preferably 20×$10^{-3}$ Vm/N or more, more preferably 25×$10^{-3}$ Vm/N or more, and even more preferably 30×$10^{-3}$ Vm/N or more.

Figure 6:
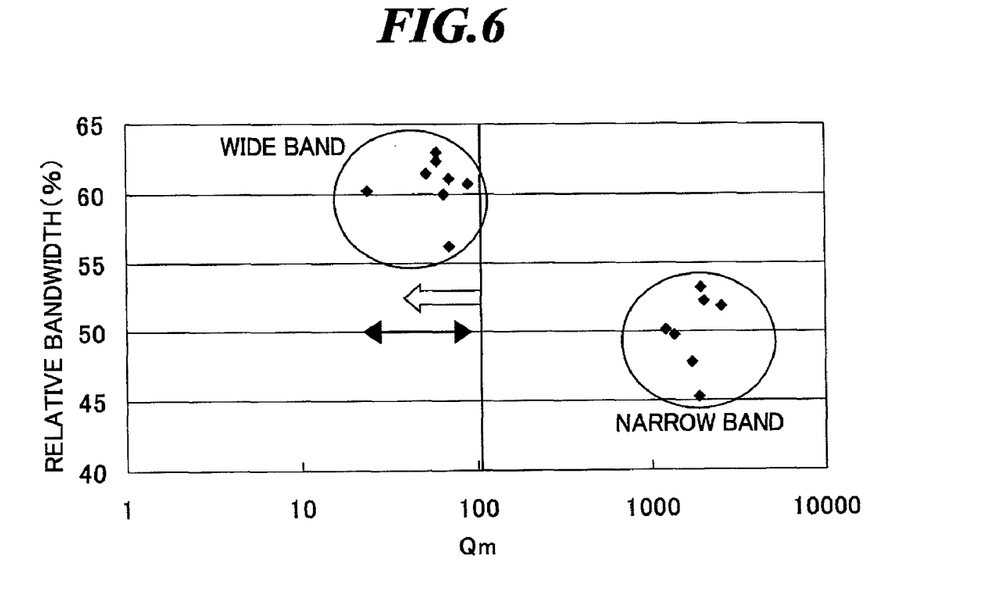
FIG. 6 shows a relationship between the mechanical quality factor Qm and the relative bandwidth.

FIG. 6 shows a relationship between the mechanical quality factor Qm and the relative bandwidth. As shown in FIG. 6, the relative bandwidth has a tendency to be wider as the mechanical quality factor Qm is smaller. When a piezoelectric material having Qm of 100 or less, nearly sufficient wide band characteristics can be achieved. More preferably, it is recommended to use a piezoelectric material having Qm of 90 or less, even more preferably a piezoelectric material having Qm of 70 or less.

Next, a structure of an ultrasonic probe according to the second embodiment of the present invention will be explained. The ultrasonic probe according to the second embodiment uses multilayered piezoelectric vibrators in a one-dimensional vibrator array of the ultrasonic probe according to the first embodiment.

Figure 7:
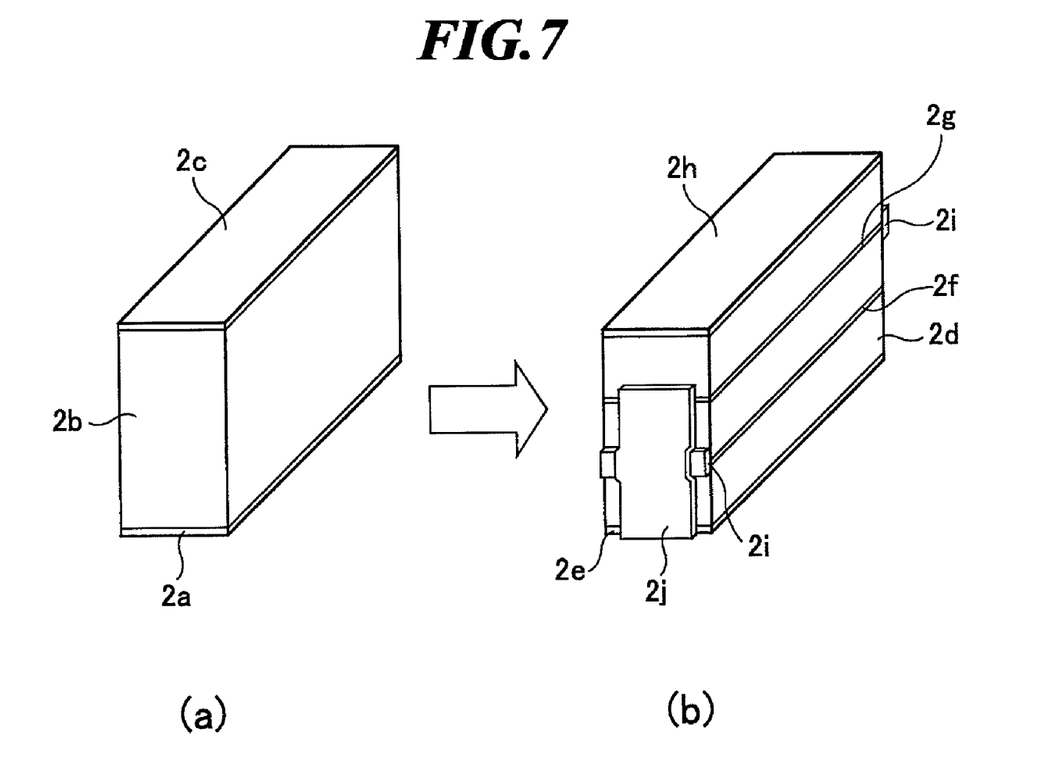
FIG. 7 shows piezoelectric vibrator structures in comparison between the first embodiment and the second embodiment of the present invention.

FIG. 7 shows piezoelectric vibrator structures in comparison between the first embodiment and the second embodiment of the present invention. In the first embodiment, as shown in FIG. 7(a), the piezoelectric vibrator has a single layer structure including an individual electrode 2a, a piezoelectric material 2b formed on the individual electrode 2a, and a common electrode 2c formed on the piezoelectric material 2b.

On the other hand, in the second embodiment, as shown in FIG. 7(b), the piezoelectric vibrator has a multilayered structure including plural piezoelectric material layers 2d formed of PZT or the like, a lower electrode layer 2e, internal electrode layers 2f and 2g alternately inserted between the plural piezoelectric material layers 2d, an upper electrode layer 2h, insulating films 2i, a front side electrode 2j, and a rear side electrode (not shown).

Here, the lower electrode layer 2e is connected to the front side electrode 2j and insulated from the rear side electrode. The upper electrode layer 2h is connected to the rear side electrode and insulated from the front side electrode 2j. Further, the internal electrode layer 2f is connected to the rear side electrode and insulated from the front side electrode 2j by the insulating film 2i. On the other hand, the internal electrode layer 2g is connected to the front side electrode 2j and insulated from the rear side electrode by the insulating film 2i. The plural electrodes are formed in this manner, and three sets of electrodes for applying electric fields to the three layers of piezoelectric materials are connected in parallel. The number of piezoelectric materials is not limited to three, but may be two or four or more.

In the multilayered piezoelectric vibrator, the area of opposed electrodes becomes larger than that of the single-layered element, and the electric impedance becomes lower. Therefore, the multilayered piezoelectric vibrator operates more efficiently for the applied voltage than a single-layered piezoelectric vibrator having the same size. Specifically, given that the number of piezoelectric material layers is N, the number of piezoelectric material layers of the multilayered piezoelectric vibrator is N-times that of the single-layered piezoelectric vibrator, and the thickness of each piezoelectric material layer of the multilayered piezoelectric vibrator is 1/N of that of the single-layered piezoelectric vibrator, and thereby, the electric impedance of the multilayered piezoelectric vibrator is $1/N^2$-times that of the single-layered piezoelectric vibrator. Therefore, the electric impedance of the piezoelectric vibrator can be adjusted by increasing or decreasing the number of stacked piezoelectric material layers, and thus, the electric impedance matching between the piezoelectric vibrator and a drive circuit or signal cable is easily provided so that the sensitivity can be improved. On the other hand, since the capacitance increases when the piezoelectric vibrator is multilayered, the amount of heat generation from the piezoelectric vibrator also increases. In the embodiment, the temperature rise of the ultrasonic probe is prevented by selecting a suitable piezoelectric material.

Next, a structure of an ultrasonic probe according to the third embodiment of the present invention will be explained. The ultrasonic probe according to the third embodiment is, in the ultrasonic probe according to the second embodiment, to replace the bulk piezoelectric material forming the piezoelectric material layers in each piezoelectric vibrator with a composite material of a piezoelectric material and a resin so as to form a 1-3 composite piezoelectric vibrator.

In the case of 1-3 composite, each vibrator has a rod-like shape, and the vibration mode thereof is the 33 vibration mode. The 33 vibration mode refers to a vibration mode in which a piezoelectric material poling-processed in the third direction (Z-axis direction) is applied with an electric field in the same third direction to vibrate. Generally, in a vibrator, the electromechanical coupling factor k33 in the 33 vibration mode is larger than the electromechanical coupling factor kt in the plate-like shape or the electromechanical coupling factor k33' in the bar shape, and thus, high conversion efficiency can be obtained by the rod-like vibrators.

Figure 8:
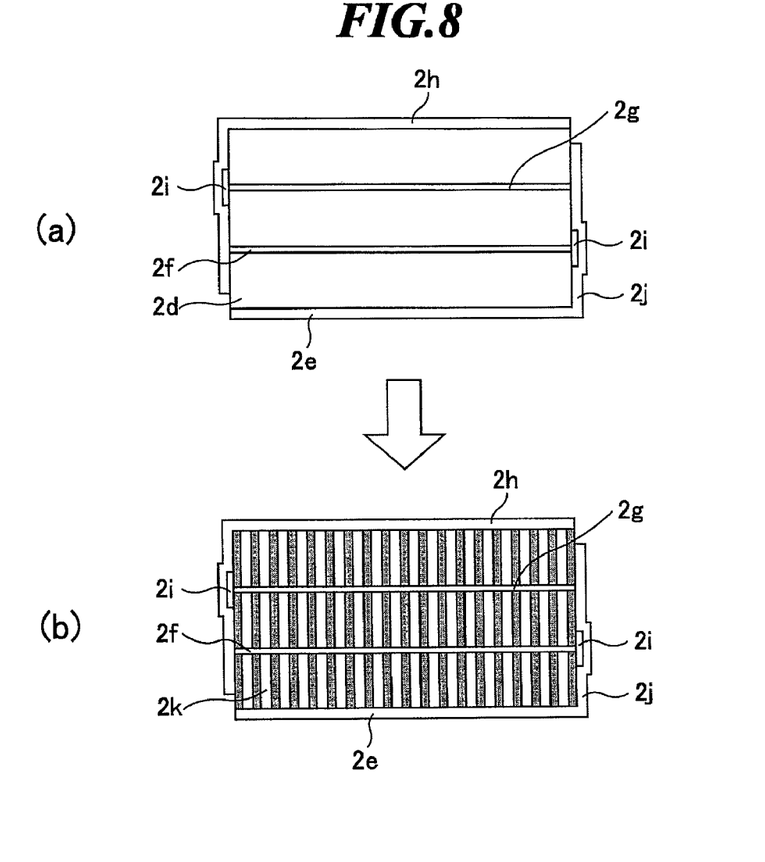
FIG. 8 shows piezoelectric vibrator structures in comparison between the second embodiment and the third embodiment of the present invention.

FIG. 8 shows piezoelectric vibrator structures in comparison between the second embodiment and the third embodiment of the present invention. In the second embodiment, as shown in FIG. 8(a), the piezoelectric material layer 2d formed of a bulk piezoelectric material is used. The acoustic impedance of the piezoelectric material layer 2d is about 30 MRayl. On the other hand, in the third embodiment, as shown in FIG. 8(b), a composite material layer 2k including a piezoelectric material and a resin is used. The acoustic impedance of the composite material layer 2k takes a value smaller than 10 MRayl and near about 1.5 MRayl as the acoustic impedance of a human body, and thus, reflection of ultrasonic waves at a boundary between the ultrasonic probe and an object to be inspected (human body) can be reduced.

Figure 9:
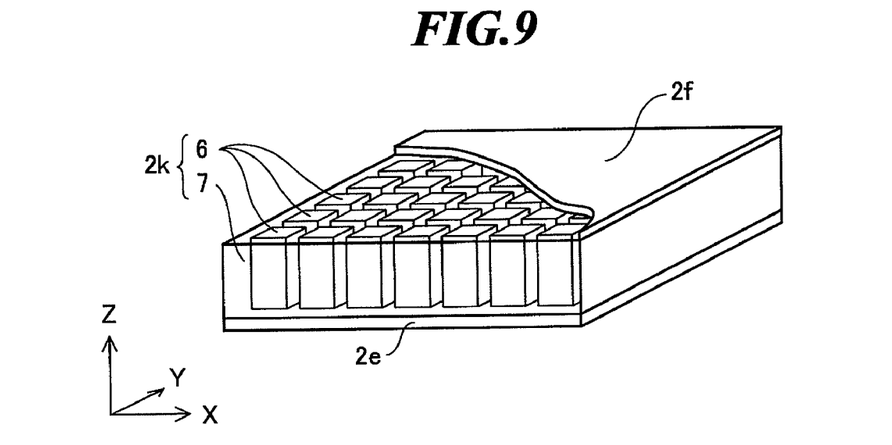
FIG. 9 is a perspective view showing a structure of the lowermost layer of a multilayered piezoelectric vibrator shown in FIG. 8(b)

FIG. 9 is a perspective view showing a structure of the lowermost layer of the multilayered piezoelectric vibrator shown in FIG. 8(b). When a voltage is applied between two electrode layers (the lower electrode layer 2e and the internal electrode layer 2f) sandwiching the composite material layer 2k, an electric field is formed in the Z-axis direction. As shown in FIG. 9, the composite material layer 2k includes plural piezoelectric materials 6 which are two-dimensionally arranged to have a longitudinal direction substantially in parallel with the Z-axis direction, and a resin (e.g., an epoxy resin) 7 filling between and around the plural piezoelectric materials 6. In the above explanation, the case of using the composite material layer in the multilayered piezoelectric vibrator has been explained, however, the composite material layer may be used in the piezoelectric vibrator having a single-layered structure as shown in FIG. 7(a).

The measurement results of the properties of the ultrasonic probes according to the second and third embodiments will be explained as below. In measurement of sensitivity and relative bandwidth, only one vibrator of a one-dimensional vibrator array is driven and ultrasonic waves are transmitted and received in a water tank, and the properties thereof are measured. The center frequency of the ultrasonic waves to be transmitted and received is 6 MHz, and an ultrasonic transmitting and receiving apparatus (Model 5900 manufactured by Panametrics) is used for generating a drive signal.

In measurement of temperature rise ΔT, the ultrasonic probe is connected to the ultrasonic diagnostic apparatus main body, the ultrasonic probe is continuously driven in a color Doppler mode as the most severe drive mode in view of temperature rise, and the surface temperature rise is measured by using a noncontact thermometer in the air at room temperature of 23° C. The surface temperature rises with time immediately after the driving of vibrator is started and nearly saturated in about 10 minutes, and thus, the temperature is measured after saturation.

Figure 10:
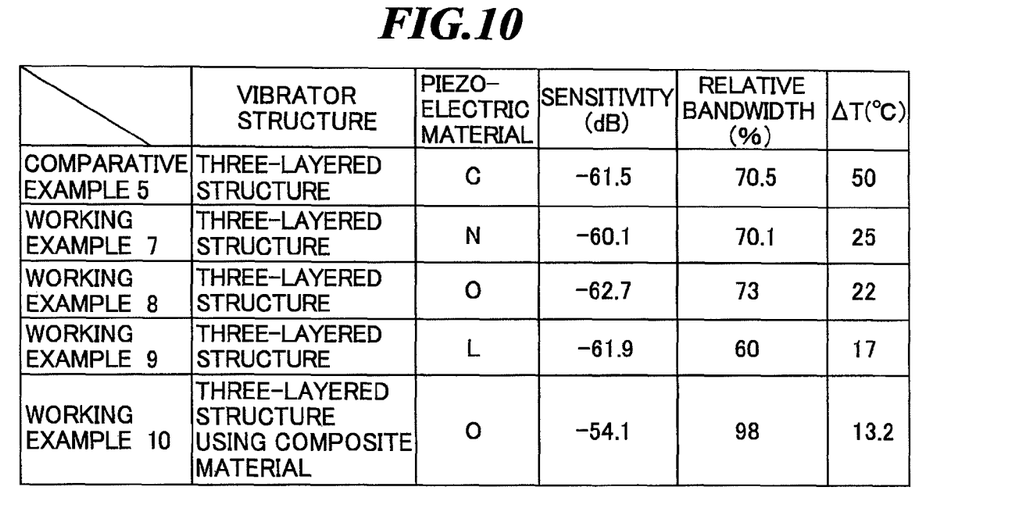
FIG. 10 shows measurement results of properties of the ultrasonic probes according to the second and third embodiments.

FIG. 10 shows measurement results of properties of the ultrasonic probes according to the second and third embodiments. In FIG. 10, vibrator structures, piezoelectric materials, transmission and reception sensitivity, relative bandwidths, and temperature rises ΔT of the ultrasonic probes in comparative example 5 and working examples 7-10 of the present invention are shown. In comparative example 5 and working examples 7-10 of the present invention, the vibrator structure is a three-layered structure, and the composite material explained in the third embodiment is used in working example 10.

In comparison between the properties of these ultrasonic probes with the properties of the ultrasonic probe having single-layered structures using the same piezoelectric materials (see FIG. 2), higher performance is realized by the three-layered structure of the vibrator, and the sensitivity is improved by about 10 dB and the relative bandwidth becomes wider by about 10%. Note that, if the vibrator has the three-layered structure, there is a problem that the temperature rise ΔT becomes three to five times compared to the single-layered vibrator.

Figure 11:
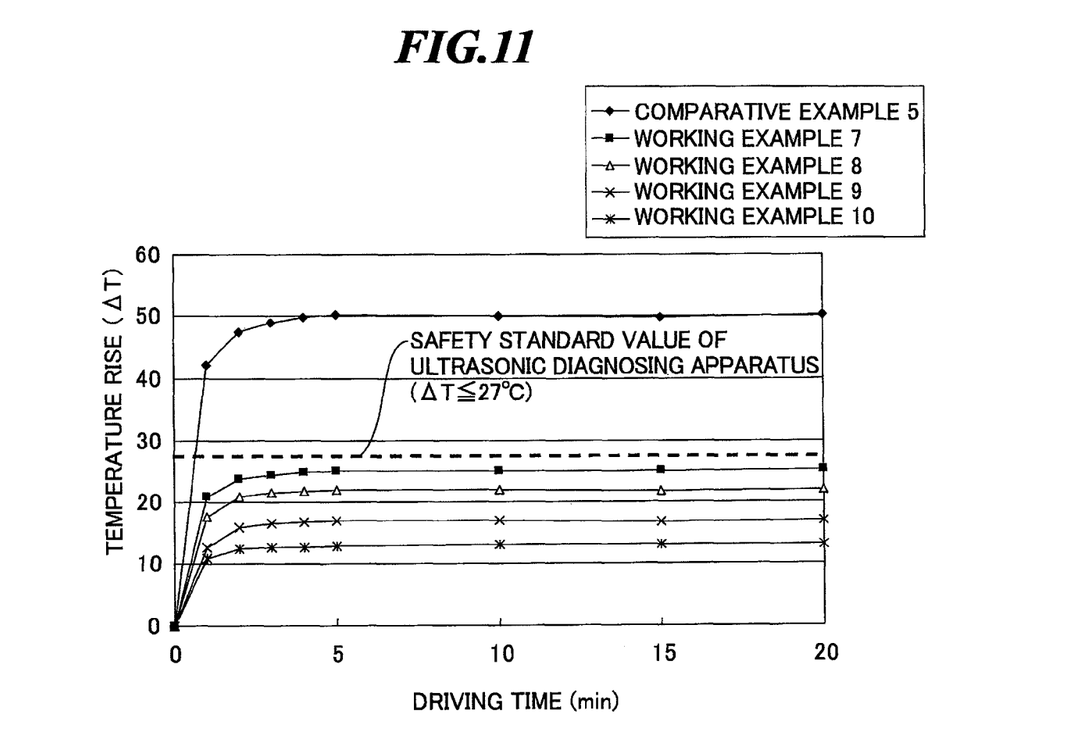
FIG. 11 shows changes in temperature rise ΔT of the ultrasonic probes according to the second and third embodiments.

FIG. 11 shows changes in temperature rise ΔT of the ultrasonic probes according to the second and third embodiments. In FIG. 11, the horizontal axis indicates driving time (min) and the vertical axis indicates temperature rise ΔT. The comparative example 5 is the ultrasonic probe having a three-layered structure using a standard piezoelectric material C, and the temperature rise ΔT reaches 50° C. and largely exceeds the safety standard (ΔT≦27° C.) of the ultrasonic diagnostic apparatus. On the other hand, according to the working examples 7-10 of the present invention, the temperature rise ΔT can be suppressed to 25° C. or less, and can satisfy the safety standard.

Referring FIG. 10 again, the working example 10 uses the same piezoelectric material as that in the working example 8, however, the composite material is formed by combining the piezoelectric material ○ and a resin to make 1-3 composite including the piezoelectric material, and thereby, the sensitivity is improved by about 9 dB and the relative bandwidth is improved by 25% compared to the working example 8. Further, the temperature rise ΔT is reduced by 8.8° C. compared to the working example 8.

In the above working examples, the case of using piezoelectric ceramics as the piezoelectric material has been explained, however, the present invention can be applied to the case of using a single crystal piezoelectric material. Further, for reduction of the surface temperature of the ultrasonic probe, a backing material having a high coefficient of thermal conductivity may be used or an acoustic matching layer or acoustic lens having a low coefficient of thermal conductivity may be used. Furthermore, using a structure for releasing heat generated in the vibrator from the backing material to the casing is effective.

Figure 12:
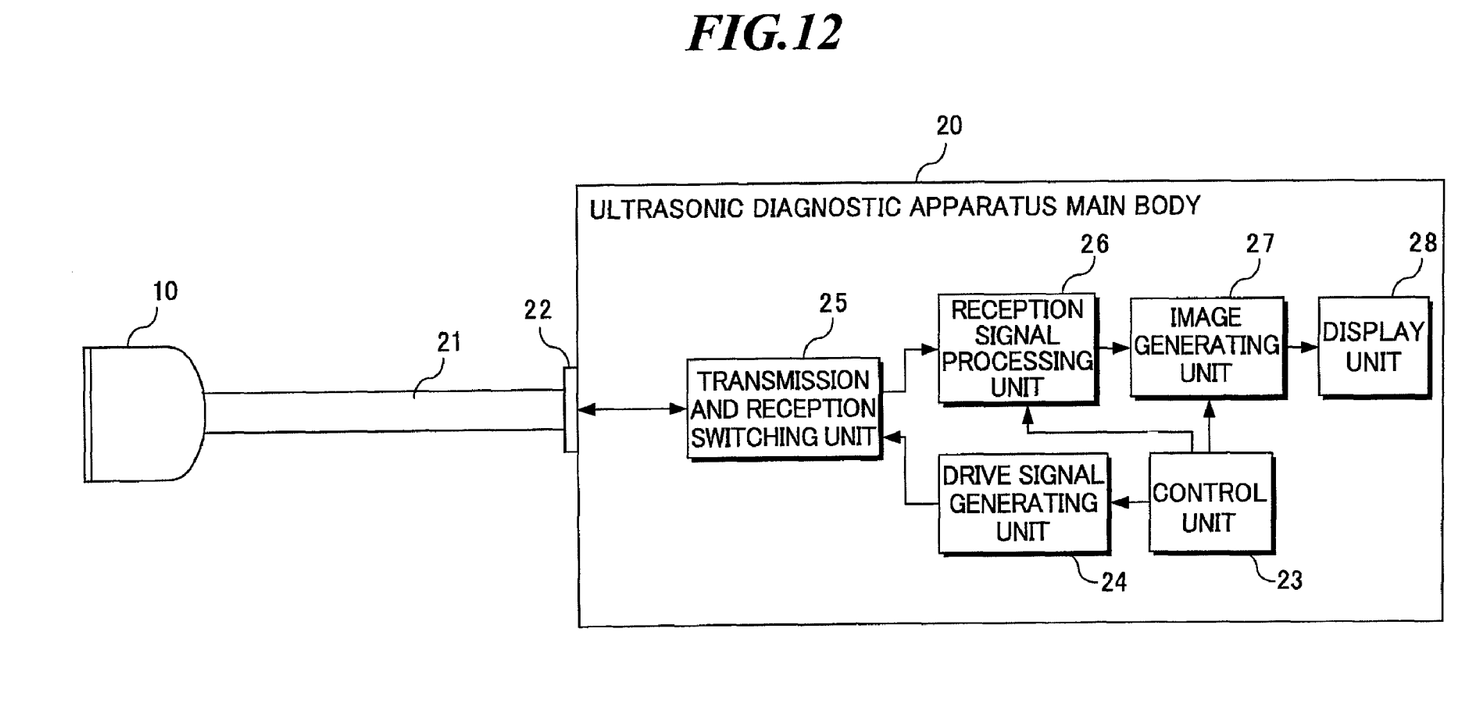
FIG. 12 shows an ultrasonic diagnostic apparatus including the ultrasonic probe according to any one of the first to third embodiments of the present invention and an ultrasonic diagnostic apparatus main body.

FIG. 12 shows an ultrasonic diagnostic apparatus including the ultrasonic probe according to any one of the first to third embodiments of the present invention and an ultrasonic diagnostic apparatus main body.

As shown in FIG. 12, the ultrasonic probe 10 is electrically connected to the ultrasonic diagnostic apparatus main body 20 via an electric cable 21 and a connector 22. The electric cable 21 transmits drive signals generated in the ultrasonic diagnostic apparatus main body 20 to the respective ultrasonic transducers (piezoelectric vibrators) and transmits reception signals outputted from the respective ultrasonic transducers to the ultrasonic diagnostic apparatus main body 20.

The ultrasonic diagnostic apparatus main body 20 includes a control unit 23 for controlling the operation of the entire ultrasonic diagnostic apparatus, a drive signal generating unit 24, a transmission and reception switching unit 25, a reception signal processing unit 26, an image generating unit 27, and a display unit 28. The drive signal generating unit 24 includes plural drive circuits (pulsers or the like), for example, and generates drive signals to be used for respectively driving the plural ultrasonic transducers. The transmission and reception switching unit 25 switches output of drive signals to the ultrasonic probe 10 and input of reception signals from the ultrasonic probe 10.

The reception signal processing unit 26 includes plural preamplifiers, plural A/D converters, and a digital signal processing circuit or CPU, for example, and performs predetermined signal processing of amplification, phase matching and addition, envelope detection, etc. on the reception signals outputted from the respective ultrasonic transducers. The image generating unit 27 generates image data representing an ultrasonic image based on the reception signals on which the predetermined signal processing has been performed. The display unit 28 displays the ultrasonic image based on thus generated image data.

Next, an ultrasonic endoscope using an ultrasonic probe according to the fourth embodiment of the present invention will be explained with reference to FIGS. 13 and 14. The ultrasonic endoscope refers to an apparatus provided with an ultrasonic transducer part (ultrasonic probe) at the leading end of an insertion part of an endoscopic examination unit for optically observing the interior of the body cavity of the object. In the fourth embodiment, piezoelectric vibrators similar to those explained in the first to third embodiments are used.

Figure 13:
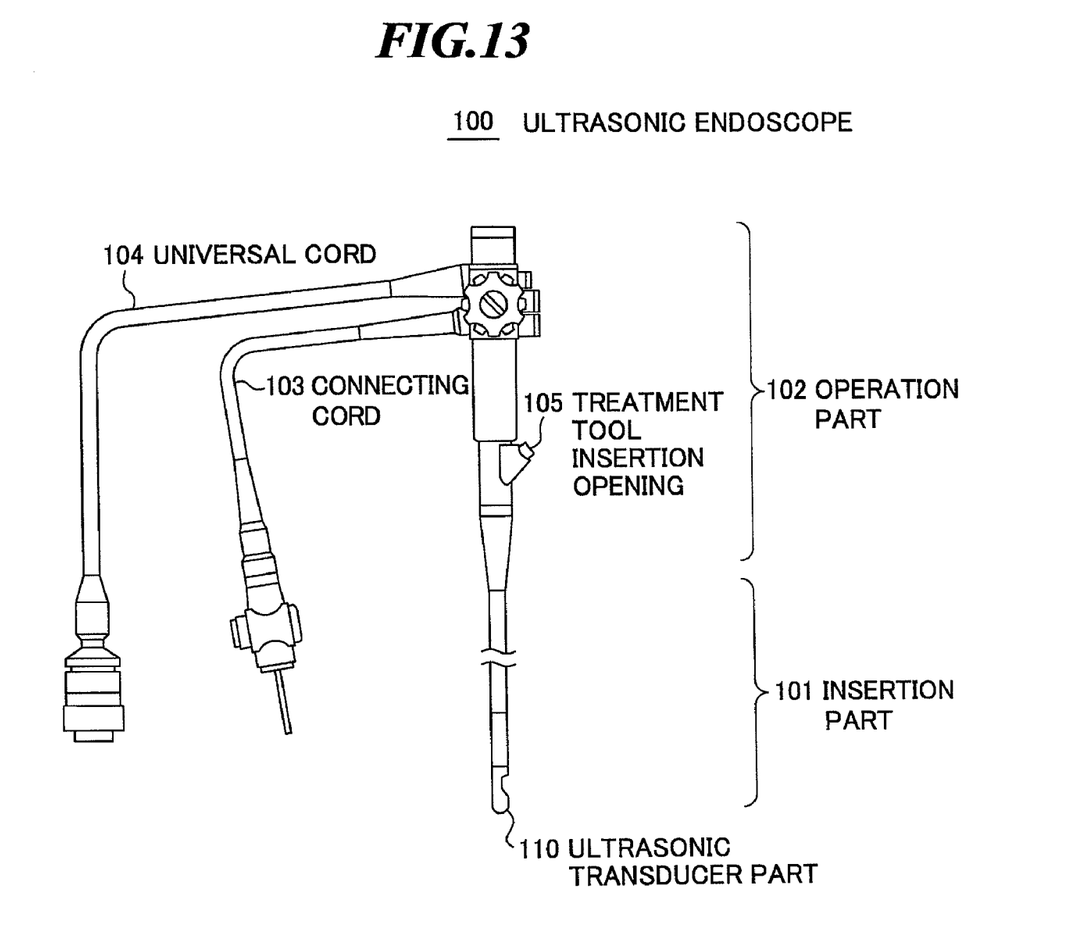
FIG. 13 is a schematic diagram showing an appearance of the ultrasonic endoscope using the ultrasonic probe according to the fourth embodiment of the present invention.

FIG. 13 is a schematic diagram showing an appearance of the ultrasonic endoscope using the ultrasonic probe according to the fourth embodiment of the present invention. As shown in FIG. 13, an ultrasonic endoscope 100 includes an insertion part 101, an operation part 102, a connecting cord 103, and a universal cord 104.

The insertion part 101 is an elongated tube formed of a material having flexibility for insertion into the body of the object. An ultrasonic transducer part (ultrasonic probe) 110 is provided at the leading end of the insertion part 101.

The operation part 102 is provided at the base end of the insertion part 101, connected to the ultrasonic endoscopic apparatus main body via the connecting cord 103, and connected to a light source unit via the universal cord 104. A treatment tool insertion opening 105 for inserting a treatment tool or the like into the insertion part 101 is provided in the operation part 102.

Figure 14:
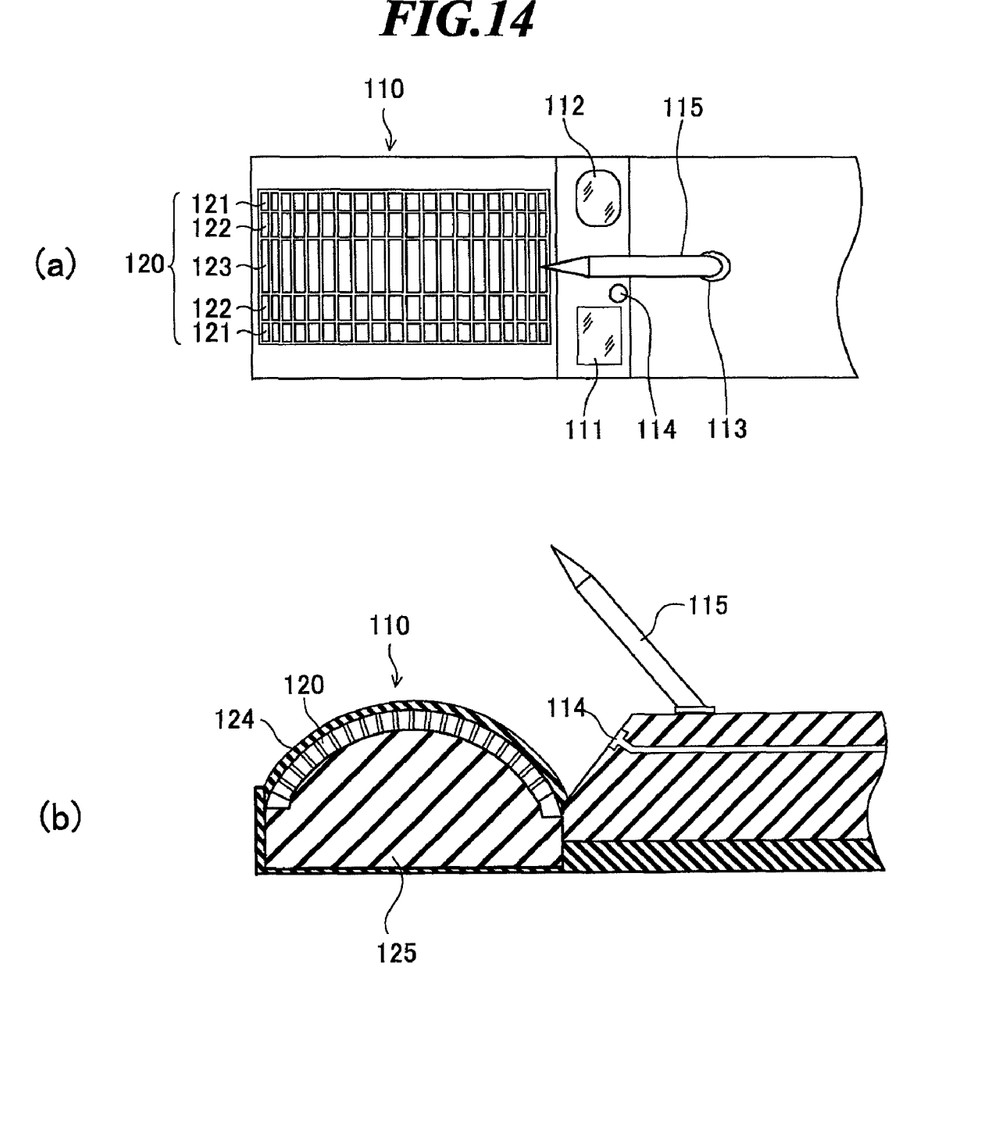
FIG. 14 is an enlarged schematic diagram showing the leading end of the insertion part of the ultrasonic endoscope shown in FIG. 13.

FIG. 14 is an enlarged schematic diagram showing the leading end of the insertion part of the ultrasonic endoscope shown in FIG. 13. FIG. 14(a) is a plan view showing the upper surface of the leading end of the insertion part 101, and FIG. 14(b) is a side sectional view showing the side surface of the leading end of the insertion part 101. In FIG. 14(a), an acoustic matching layer 124 shown in FIG. 14(b) is omitted.

As shown in FIG. 14, at the leading end of the insertion part, the ultrasonic transducer part 110, an observation window 111, an illumination window 112, a treatment tool passage opening 113, and a nozzle hole 114 are provided. A punctuation needle 115 is provided in the treatment tool passage opening 113. In FIG. 14(a), an objective lens is fit in the observation window 111, and an input end of an image guide or a solid-state image sensor such as a CCD camera is provided in the imaging position of the objective lens. These configure an observation optics. Further, an illumination lens for outputting illumination light supplied from the light source unit via a light guide is fit in the illumination window 112. These configure an illumination optics.

The treatment tool passage opening 113 is a hole for leading out a treatment tool or the like inserted from the treatment tool insertion opening 105 provided in the operation part 102 shown in FIG. 12. Various treatments are performed within a body cavity of the object by projecting the treatment tool such as the punctuation needle 115 or forceps from the hole and operating it with the operation part 102. The nozzle hole 114 is provided for injecting a liquid (water or the like) for cleaning the observation window 111 and the illumination window 112.

The ultrasonic transducer part 110 includes a convex-type multirow vibrator array 120, and the vibrator array 120 has plural ultrasonic transducers (piezoelectric vibrators) 121-

123 arranged in five rows on a curved surface. As shown in FIG. 14(b), the acoustic matching layer 124 is provided on a first surface of the vibrator array 120. An acoustic lens is provided on the acoustic matching layer 124 according to need. Further, a backing material 125 is provided on a second surface opposite to the first surface of the vibrator array 120.

In FIG. 14, the convex-type multirow array is shown as the vibrator array 120, however, a radial-type ultrasonic transducer part in which plural ultrasonic transducers are arranged on a cylindrical surface or an ultrasonic transducer part in which plural ultrasonic transducers are arranged on a spherical surface may be used. In the ultrasonic endoscope, downsizing is required, and thus, the heat generation reduction effect according to the present invention is especially effective.

Figure 15:
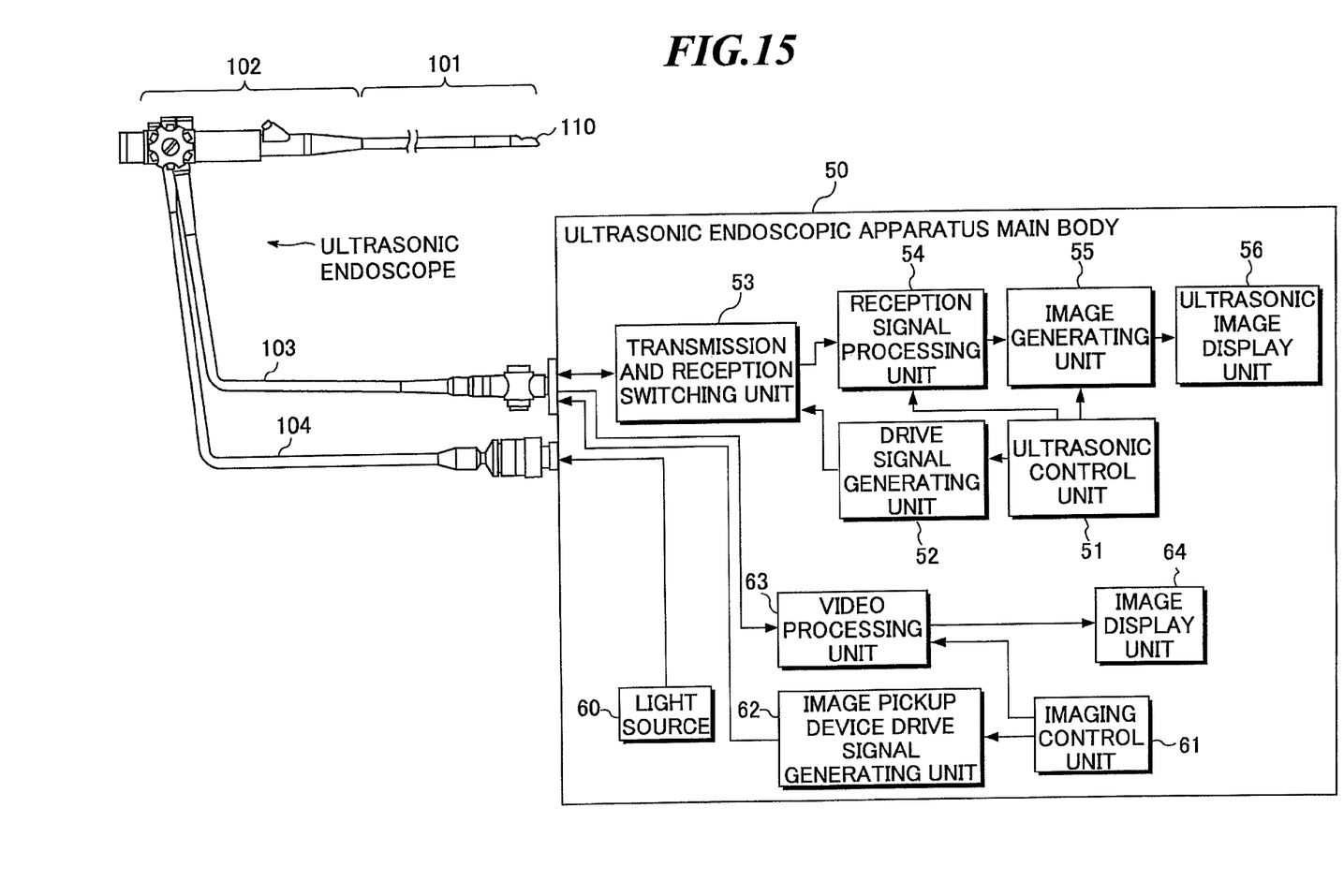
FIG. 15 shows an ultrasonic endoscopic apparatus including the ultrasonic endoscope shown in FIG. 13 and an ultrasonic endoscopic apparatus main body.

FIG. 15 shows an ultrasonic endoscopic apparatus including the ultrasonic endoscope shown in FIG. 13 and an ultrasonic endoscopic apparatus main body. The plural ultrasonic transducers (piezoelectric vibrators) included in the ultrasonic transducer part (ultrasonic probe) 110 of the ultrasonic endoscope 100 are electrically connected to the ultrasonic endoscopic apparatus main body 50 by plural shield lines via the insertion part 101, the operation part 102, and the connecting cord 103. Those shield lines transmit drive signals generated in the ultrasonic endoscopic apparatus main body 50 to the respective ultrasonic transducers and transmit reception signals outputted from the respective ultrasonic transducers to the ultrasonic endoscopic apparatus main body 50.

The ultrasonic endoscopic apparatus main body 50 includes an ultrasonic control unit 51, a drive signal generating unit 52, a transmission and reception switching unit 53, a reception signal processing unit 54, an image generating unit 55, an ultrasonic image display unit 56, a light source 60, an imaging control unit 61, an image pickup device drive signal generating unit 62, a video processing unit 63, and an image display unit 64.

The ultrasonic control unit 51 controls the imaging operation using the ultrasonic transducer part 110. The drive signal generating unit 52 includes plural drive circuits (pulsers or the like), for example, and generates drive signals to be used for respectively driving the plural ultrasonic transducers. The transmission and reception switching unit 53 switches output of drive signals to the ultrasonic transducer part 110 and input of reception signals from the ultrasonic transducer part 110.

The reception signal processing unit 54 includes plural preamplifiers, plural A/D converters, and a digital signal processing circuit or CPU, for example, and performs predetermined signal processing of amplification, phase matching and addition, envelope detection, etc. on the reception signals outputted from the respective ultrasonic transducers. The image generating unit 55 generates image data representing an ultrasonic image based on the reception signals on which the predetermined signal processing has been performed. The display unit 56 displays the ultrasonic image based on thus generated image data.

The light source 60 emits light to be used for illumination of the object. The light outputted from the light source 60 illuminates the object via the universal cord 104 through the illumination window 112 of the insertion part 101 (FIG. 14(a)). The illuminated object is imaged by an image pickup device through the observation window 111 of the insertion part 101 (FIG. 14(a)), and video signals outputted from the image pickup device are received by the video processing unit 63 of the ultrasonic endoscopic apparatus main body 50 via the connecting cord 103.

The imaging control unit 61 controls imaging operation using the image pickup device. The image pickup device drive signal generating unit 62 generates drive signals to be supplied to the image pickup device. The video processing unit 63 generates image data based on the video signals received from the image pickup device. The image display unit 64 receives the image data from the video processing unit 63 and displays images of the object.

The invention claimed is:

1. An ultrasonic probe comprising:
   at least one vibrator for transmitting and receiving ultrasonic waves, said at least one vibrator including a piezoelectric material in which a piezoelectric strain constant (d33) is not larger than 500 pm/V to reduce heat generation and a product of the piezoelectric strain constant (d33) and a piezoelectric voltage constant (g33) is not less than $7000 \times 10^{-15}$ m$^2$/N to maintain transmission and reception sensitivity higher than a predetermined value;
   at least one acoustic matching layer provided on a first surface of said at least one vibrator; and
   a backing material provided on a second surface opposite to the first surface of said at least one vibrator.

2. The ultrasonic probe according to claim 1, wherein the piezoelectric voltage constant (g33) of said piezoelectric material is not less than $20 \times 10^{-3}$ Vm/N to improve reception sensitivity.

3. The ultrasonic probe according to claim 1, wherein a mechanical quality factor (Qm) of said piezoelectric material is not larger than 100 to reduce heat generation and maintain a relative bandwidth higher than a predetermined value.

4. The ultrasonic probe according to claim 1, wherein said at least one vibrator includes a composite material layer, and a first electrode layer and a second electrode layer provided on both ends of said composite material layer, and said composite material layer includes plural piezoelectric materials having a longitudinal direction substantially in parallel with a direction of an electric field formed when a voltage is applied between said first electrode layer and said second electrode layer, and a resin filling between said plural piezoelectric materials.

5. The ultrasonic probe according to claim 1, wherein said at least one vibrator includes a first electrode layer and a second electrode layer, and plural piezoelectric material layers alternately stacked with at least one internal electrode layer between said first electrode layer and said second electrode layer.

6. The ultrasonic probe according to claim 1, wherein said at least one vibrator includes a first electrode layer and a second electrode layer, and plural composite material layers alternately stacked with at least one internal electrode layer between said first electrode layer and said second electrode layer, and each of said plural composite material layers includes plural piezoelectric materials having a longitudinal direction substantially in parallel with a direction of an electric field formed when a voltage is applied between two electrode layers sandwiching said plural composite material layers, and a resin filling between said plural piezoelectric materials.

7. An ultrasonic diagnostic apparatus comprising:
   an ultrasonic probe having at least one vibrator for transmitting and receiving ultrasonic waves, said at least one vibrator including a piezoelectric material in which a piezoelectric strain constant (d33), is not larger than 500 pm/V to reduce heat generation and a product of the piezoelectric strain constant (d33) and a piezoelectric voltage constant (g33) is not less than $7000 \times 10^{-15}$ m$^2$/N to maintain transmission and reception sensitivity higher than a predetermined value;

drive signal supply means for supplying at least one drive signal to said at least one vibrator; and signal processing means for processing at least one reception signal outputted from said at least one vibrator to generate image data representing an ultrasonic image.

8. An ultrasonic endoscopic apparatus comprising:

an ultrasonic endoscope having at least one vibrator for transmitting and receiving ultrasonic waves, said at least one vibrator including a piezoelectric material in which a piezoelectric strain constant (d33) is not larger than 500 pm/V to reduce heat generation and a product of the piezoelectric strain constant (d33) and a piezoelectric voltage constant (g33) is not less than $7000 \times 10^{-15}$ m$^2$/N to maintain transmission and reception sensitivity higher than a predetermined value;

drive signal supply means for supplying at least one drive signal to said at least one vibrator; and signal processing means for processing at least one reception signal outputted from said at least one vibrator to generate image data representing an ultrasonic image.

9. The ultrasonic probe according to claim 1, wherein said piezoelectric material comprises a compound selected from the group consisting of:

(i) $(Pb_{0.95}Sr_{0.05})(Zr_{0.54}Ti_{0.46})O_3:Mn_{0.006},Sb_{0.006},Nb_{0.007}$;

(ii) $Pb(Zr_{0.51}Ti_{0.49})O_3:Nb_{0.1},Mn_{0.015},Co_{0.016}$;

(iii) $Pb(Zr_{0.51}Ti_{0.49})O_3:Nb_{0.05},Mn_{0.017},Ag_{0.011},Sr_{0.054}$;

(iv) $(Pb_{0.96}Ba_{0.03}Sr_{0.01})(Zr_{0.54}Ti_{0.46})O_3:Sb_{0.006},Nb_{0.007}$;

(v) $(Pb_{0.94}Ba_{0.02}Sr_{0.04})(Zr_{0.53}Ti_{0.47})O_3:Nb_{0.016},Sb_{0.007}$; and (vi) $(Pb_{0.95}Sr_{0.05})(Zr_{0.53}Ti_{0.47})O_3:Nb_{0.025}$.

10. The ultrasonic diagnostic apparatus according to claim 7, wherein said piezoelectric material comprises a compound selected from the group consisting of:

(i) $(Pb_{0.95}Sr_{0.05})(Zr_{0.54}Ti_{0.46})O_3:Mn_{0.006},Sb_{0.006},Nb_{0.007}$;

(ii) $Pb(Zr_{0.51}Ti_{0.49})O_3:Nb_{0.1},Mn_{0.015},Co_{0.016}$;

(iii) $Pb(Zr_{0.51}Ti_{0.49})O_3:Nb_{0.05},Mn_{0.017},Ag_{0.011},Sr_{0.054}$;

(iv) $(Pb_{0.96}Ba_{0.03}Sr_{0.01})(Zr_{0.54}Ti_{0.46})O_3:Sb_{0.006},Nb_{0.007}$;

(v) $(Pb_{0.94}Ba_{0.02}Sr_{0.04})(Zr_{0.53}Ti_{0.47})O_3:Nb_{0.016},Sb_{0.007}$; and (vi) $(Pb_{0.95}Sr_{0.05})(Zr_{0.53}Ti_{0.47})O_3:Nb_{0.025}$.

11. The ultrasonic endoscopic apparatus according to claim 8, wherein said piezoelectric material comprises a compound selected from the group consisting of:

(i) $(Pb_{0.95}Sr_{0.05})(Zr_{0.54}Ti_{0.46})O_3:Mn_{0.006},Sb_{0.006},Nb_{0.007}$;

(ii) $Pb(Zr_{0.51}Ti_{0.49})O_3:Nb_{0.1},Mn_{0.015},Co_{0.016}$;

(iii) $Pb(Zr_{0.51}Ti_{0.49})O_3:Nb_{0.05},Mn_{0.017},Ag_{0.011},Sr_{0.054}$;

(iv) $(Pb_{0.96}Ba_{0.03}Sr_{0.01})(Zr_{0.54}Ti_{0.46})O_3:Sb_{0.006},Nb_{0.007}$;

(v) $(Pb_{0.94}Ba_{0.02}Sr_{0.04})(Zr_{0.53}Ti_{0.47})O_3:Nb_{0.016},Sb_{0.007}$; and (vi) $(Pb_{0.95}Sr_{0.05})(Zr_{0.53}Ti_{0.47})O_3:Nb_{0.025}$.

* * * * *